US008535559B2

(12) United States Patent
Flynn et al.

(10) Patent No.: US 8,535,559 B2
(45) Date of Patent: *Sep. 17, 2013

(54) NITROGEN-CONTAINING FLUOROKETONES FOR HIGH TEMPERATURE HEAT TRANSFER

(75) Inventors: Richard M. Flynn, Mahtomedi, MN (US); Michael G. Costello, Afton, MN (US); Michael J. Bulinski, Houlton, WI (US); Daniel R. Vitcak, Cottage Grove, MN (US); Phillip E. Tuma, Fanbault, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 554 days.

This patent is subject to a terminal disclaimer.

(21) Appl. No.: 12/732,608

(22) Filed: Mar. 26, 2010

(65) Prior Publication Data
US 2011/0232870 A1 Sep. 29, 2011

(51) Int. Cl.
*C09K 5/00* (2006.01)
(52) U.S. Cl.
USPC ............................. 252/73; 252/74; 568/683
(58) Field of Classification Search
None
See application file for complete search history.

(56) References Cited

U.S. PATENT DOCUMENTS

| | | | |
|---|---|---|---|
| 2,713,593 A | 7/1955 | Brice | |
| 4,067,884 A | 1/1978 | Martini | |
| 4,136,121 A | 1/1979 | Martini | |
| 4,670,307 A | 6/1987 | Onishi | |
| 5,210,238 A | 5/1993 | Anderson | |
| 5,962,390 A | 10/1999 | Flynn | |
| 6,374,907 B1 | 4/2002 | Tousignant et al. | |
| 6,953,082 B2 | 10/2005 | Costello | |
| 7,124,809 B2 | 10/2006 | Rosenfeld | |
| 7,128,133 B2 | 10/2006 | Costello | |
| 7,385,089 B2 * | 6/2008 | Costello et al. | ............... 568/413 |
| 7,390,427 B2 | 6/2008 | Costello | |
| 2007/0102070 A1 | 5/2007 | Tuma | |
| 2007/0102140 A1 | 5/2007 | Tuma | |
| 2007/0267464 A1 | 11/2007 | Vitcak | |
| 2008/0139683 A1 | 6/2008 | Flynn | |
| 2009/0183856 A1 | 7/2009 | Bulinski | |
| 2009/0269521 A1 | 10/2009 | Tuma | |
| 2010/0108934 A1 | 5/2010 | Flynn | |
| 2010/0263885 A1 | 10/2010 | Tuma | |

FOREIGN PATENT DOCUMENTS

| | | |
|---|---|---|
| JP | 2005 126480 A | 5/2005 |
| WO | WO 2007/136948 | 11/2007 |

OTHER PUBLICATIONS

Banks, "Preparation, Properties and Industrial Applications of Organofluorine Compounds", pp. 19-43, Halsted Press, New York, 1982.
EPA-430-R-06-901, "Uses and Emissions of Liquid PFC Heat Transfer Fluids From the Electronics Sector", pp. 1-37.
Marchionni, "The Comparison of Thermal Stability of Some Hydrofluoroethers and Hydrofluoropolyethers", *Journal of Fluorine Chemistry*, 125, 2004, pp. 1081-1086.
U.S. Appl. No. 12/571,542, entitled, "Appartus Including Hydrofluoroether with High Temperature Stability and Uses Thereof", filed Oct. 1, 2009.

* cited by examiner

*Primary Examiner* — Necholus Ogden, Jr.
(74) *Attorney, Agent, or Firm* — Stephen F. Wolf; Adam Bramwell

(57) ABSTRACT

Nitrogen-containing fluorochemical ketones are provided that can be useful in apparatuses that includes a device and a mechanism for transferring heat. The provided fluorochemical ketones are stable at temperatures above 170° C., are environmentally friendly, and are economical to produce. The provided apparatuses can be useful for vapor phase soldering of electronic devices.

22 Claims, No Drawings

NITROGEN-CONTAINING FLUOROKETONES FOR HIGH TEMPERATURE HEAT TRANSFER

FIELD

This disclosure relates to apparatuses and methods that include nitrogen-containing fluoroketones as heat-transfer fluids.

BACKGROUND

Presently various fluids are used for heat transfer. The suitability of the heat-transfer fluid depends upon the application process. For example, some electronic applications require a heat-transfer fluid which is inert, has a high dielectric strength, has low toxicity, good environmental properties, and good heat transfer properties over a wide temperature range. Other applications require precise temperature control and thus the heat-transfer fluid is required to be a single phase over the entire process temperature range and the heat-transfer fluid properties are required to be predictable, i.e., the composition remains relatively constant so that the viscosity, boiling point, etc. can be predicted so that a precise temperature can be maintained and so that the equipment can be appropriately designed.

Perfluorocarbons, perfluoropolyethers (PFPEs), and some hydrofluoroethers have been used for heat-transfer. Perfluorocarbons (PFCs) can have high dielectric strength and high resistivity. PFCs can be non-flammable and are generally mechanically compatible with materials of construction, exhibiting limited solvency. Additionally, PFCs generally exhibit low toxicity and good operator friendliness. PFCs can be manufactured in such a way as to yield a product that has a narrow molecular weight distribution. PFCs and PFPEs can exhibit one important disadvantage, however, and that is long environmental persistence which can give rise to high global warming potentials. Materials currently used as heat-transfer fluids for cooling electronics or electrical equipment include PFCs, PFPEs, silicone oils, and hydrocarbon oils. Each of these heat-transfer fluids has some disadvantage. PFCs and PFPEs may be environmentally persistent. Silicone oils and hydrocarbon oils are typically flammable.

Perfluoroketone compounds comprise a class of commercially valuable chemical compounds that exhibit a wide range of properties. The compounds as a class are neutral and, in some cases, are surprisingly inert, thermally stable, and hydrolytically stable. Such properties have made them useful as heat transfer agents, as lubricants, and even as fire extinguishing agents.

SUMMARY

There continues to be a need for heat transfer fluids which are suitable for the high temperature needs of the marketplace such as, for example, use in vapor phase soldering. There is also a continuing need for heat transfer fluids that have thermal stability at the temperature of use and that have a short atmospheric lifetime so that they have a reduced global warming potential. The provided fluorochemical ketones are easy to manufacture, perform well as heat transfer fluids at high temperature, and yield products that can be consistently made. Additionally, they can be thermally stable at use temperatures, typically above 170° C., and have relatively shorter atmospheric lifetimes than conventional materials. There is also a need for apparatuses and processes for high temperature heat transfer that include these fluorochemical ketones.

In this disclosure:

"in-chain heteroatom" refers to an atom other than carbon (for example, oxygen and nitrogen) that is bonded to carbon atoms in a carbon chain so as to form a carbon-heteroatom-carbon chain;

"device" refers to an object or contrivance which is heated, cooled, or maintained at a predetermined temperature;

"inert" refers to chemical compositions that are generally not chemically reactive under normal conditions of use;

"mechanism" refers to a system of parts or a mechanical appliance; and

"perfluoro-" (for example, in reference to a group or moiety, such as in the case of "perfluoroalkylene" or "perfluoroalkylcarbonyl" or "perfluorinated") means completely fluorinated such that, except as may be otherwise indicated, there are no carbon-bonded hydrogen atoms replaceable with fluorine;

"tertiary nitrogen" refers to a nitrogen atom with three substituents other than hydrogen; and "terminal" refers to a moiety or chemical group that is at the end of a molecule or has only one group attached to it.

In one aspect, a fluorochemical nitrogen-containing diketone compound is provided that includes a first terminal, branched perfluoroalkylcarbonyl group in which said perfluoroalkyl group has from 3 to 10 in-chain carbon atoms which can include, optionally, one or more in-chain oxygen atoms; at least one linear, branched, or cyclic perfluoroalkylene segment having 4 or more in-chain carbon or nitrogen atoms attached to the first terminal, branched perfluoroalkylcarbonyl group, said perfluoroalkylene segment containing one or more in-chain tertiary nitrogen atoms, and a second terminal, branched perfluoroalkylcarbonyl group in which said perfluoroalkyl group has from 3 to 10 in-chain carbon atoms which can include, optionally, one or more in-chain oxygen atoms, wherein the second perfluoroalkylcarbonyl group is attached to the perfluoroalkylene segment. Typically, the provided fluorochemical diketones have a boiling point at ambient pressure of 170° C. or greater.

In another aspect, a fluorochemical nitrogen-containing monoketone compound is provided that comprises a first terminal, substituted or unsubstituted cyclic perfluoroalkyl group in which said cyclic perfluoroalkyl group contains a perfluoropiperazinyl, perfluoropiperidinyl, or perfluoropyrrolidinyl group which said groups may be, optionally, substituted with a perfluoroalkyl group of 1 to 4 carbons or unsubstituted; a linear or branched perfluoroalkylene segment attached to the first terminal cyclic perfluoroalkyl group which has from 1 to 4 carbon atoms and a second terminal, branched heptafluoroisopropylcarbonyl group.

In another aspect, a compound is provided that has the formula,

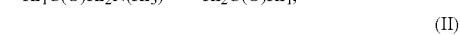

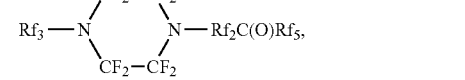

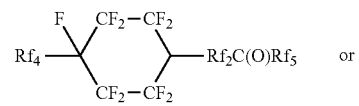

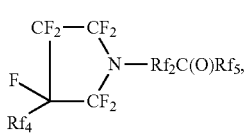

(IV)

wherein $Rf_1$ represents a perfluoroalkyl group of 3 to 10 carbon atoms that is branched or cyclic or a combination thereof, $Rf_2$ is a linear or branched perfluorinated alkylene group of 1 to 4 carbons, $Rf_3$ is a linear or branched perfluoroalkyl group of 1 to 4 carbons or —$Rf_2C(O)Rf_5$, $Rf_4$ is F— or a linear or branched perfluoroalkyl group of 1 to 4 carbons, and $Rf_5$ is —$CF(CF_3)_2$. In some embodiments, $Rf_1$ can include at least one in-chain oxygen atom.

In another aspect, an apparatus for heat transfer is provided that includes a device; and a mechanism for transferring heat to or from the device, the mechanism comprising a heat transfer fluid that includes a fluorochemical nitrogen-containing diketone compound comprising a first terminal, branched perfluoroalkylcarbonyl group in which said perfluoroalkyl group has from 3 to 10 in-chain carbon atoms which can include, optionally, one or more in-chain oxygen atoms; at least one linear, branched, or cyclic perfluoroalkylene segment having 4 or more in-chain carbon or nitrogen atoms attached to the first terminal, branched perfluoroalkylcarbonyl group, said perfluoroalkylene segment containing one or more in-chain tertiary nitrogen atoms, and a second terminal, branched perfluoroalkylcarbonyl group in which said perfluoroalkyl group has from 3 to 10 in-chain carbon atoms which can include, optionally, one or more in-chain oxygen atoms, wherein the second perfluoroalkylcarbonyl group is attached to the perfluoroalkylene segment or, optionally a fluorochemical nitrogen-containing monoketone compound that comprises a first terminal, substituted or unsubstituted cyclic perfluoroalkyl group in which said cyclic perfluoroalkyl group contains a perfluoropiperazinyl, perfluoropiperidinyl or perfluoropyrrolidinyl group which said groups may be, optionally, substituted with a perfluoroalkyl group of 1-4 carbons or unsubstituted; a linear or branched perfluoroalkylene segment attached to the first terminal cyclic perfluoroalkyl group which has from 1 to 4 carbon atoms and a second terminal, branched heptafluoroisopropylcarbonyl group. The device can be an electronic component. The mechanism transfers heat to or from the device and includes a fluorochemical ketone. The apparatus can be used, for example for vapor phase soldering of electronic components.

Finally, in another aspect, a method of transferring heat is provided that includes providing a device and transferring heat to or from the device using a mechanism, the mechanism comprising: a heat transfer fluid, wherein the heat transfer fluid includes a fluorochemical ketone compound that includes a first terminal, branched perfluoroalkylcarbonyl group in which said perfluoroalkyl group has from 3 to 10 in-chain carbon atoms which can include, optionally, one or more in-chain oxygen atoms; at least one linear, branched, or cyclic perfluoroalkylene segment having 4 or more in-chain carbon or nitrogen atoms attached to the first terminal, branched perfluoroalkylcarbonyl group, said perfluoroalkylene segment containing one or more in-chain tertiary nitrogen atoms, and a second terminal, branched perfluoroalkylcarbonyl group in which said perfluoroalkyl group has from 3 to 10 in-chain carbon atoms which can include, optionally, one or more in-chain oxygen atoms, wherein the second perfluoroalkylcarbonyl group is attached to the perfluoroalkylene segment or, optionally a fluorochemical nitrogen-containing monoketone compound that comprises a first terminal, substituted or unsubstituted cyclic perfluoroalkyl group in which said cyclic perfluoroalkyl group contains a perfluoropiperazinyl, perfluoropiperidinyl, or perfluoropyrrolidinyl group which said groups may be, optionally, substituted with a perfluoroalkyl group of 1 to 4 carbons or unsubstituted; a linear or branched perfluoroalkylene segment attached to the first terminal cyclic perfluoroalkyl group which has from 1 to 4 carbon atoms and a second terminal, branched heptafluoroisopropylcarbonyl group.

The provided nitrogen-containing fluorochemical mono- and diketones provide compounds that can be useful in heat transfer fluids. The provided fluorochemical ketones have surprisingly good thermal stability. They also have high dielectric strength, low electrical conductivity, chemical inertness, and good environmental properties. The provided fluorochemical ketones can also be useful in vapor phase soldering.

The above summary is not intended to describe each disclosed embodiment of every implementation of the present invention. The detailed description which follows more particularly exemplifies illustrative embodiments.

DETAILED DESCRIPTION

In the following description, it is to be understood that other embodiments are contemplated and may be made without departing from the scope or spirit of the present invention. The following detailed description, therefore, is not to be taken in a limiting sense.

Unless otherwise indicated, all numbers expressing feature sizes, amounts, and physical properties used in the specification and claims are to be understood as being modified in all instances by the term "about." Accordingly, unless indicated to the contrary, the numerical parameters set forth in the foregoing specification and attached claims are approximations that can vary depending upon the desired properties sought to be obtained by those skilled in the art utilizing the teachings disclosed herein. The use of numerical ranges by endpoints includes all numbers within that range (e.g. 1 to 5 includes 1, 1.5, 2, 2.75, 3, 3.80, 4, and 5) and any range within that range.

There continues to be a need for heat transfer fluids which are especially suitable for the high temperature needs of the marketplace such as for example in vapor phase soldering. In such an application temperatures of between 170° C. and 250° C. are typically used with 200° C. being particularly useful for soldering applications using a lead based solder and 230° C. useful for the higher melting lead free solders. At present the materials used in this application are of the perfluoropolyether class. In the past, certain perfluorinated amines for this application area have been marketed. Perfluoropolyethers, while having the required thermal stability at the temperatures employed, also have as a drawback that they are very environmentally persistent with extremely long atmospheric lifetimes and concomitant high global warming potentials due to their high fluorine content. As such, there is a need for new materials which have a much shorter atmospheric lifetime and yet still possess sufficient stability to be useful in vapor phase soldering as well as in other high temperature heat transfer applications.

Some hydrofluoroethers have been disclosed as heat-transfer fluids. Exemplary hydrofluoroethers can be found in U.S. patent application Ser. No. 12/263,661, entitled "Methods of Making Fluorinated Ethers, Fluorinated Ethers and Uses Thereof", filed Nov. 3, 2008, and in U.S. Pat. Publ. Nos. 2007/0267464 (Vitcak et al.) and 2008/0139683 (Flynn et al.), and U.S. Pat. Nos. 7,128,133 and 7,390,427 (Costello et al.). However, the need exists for a heat-transfer fluid which is inert, has high dielectric strength, low electrical conductivity, chemical inertness, thermal stability and effective heat transfer, is liquid over a wide temperature range, has good heat-transfer properties over a wide range of temperatures and also has a reasonably short atmospheric lifetime so that its global warming potential is relatively low.

Perfluorinated ketones of suitable structure, having boiling points of at least 170° C., are believed to possess the required stability as well as the necessary short atmospheric lifetime and hence low global warming potential to make them viable candidates for these high temperature heat transfer applications. For example, a low molecular weight ketone, $C_2F_5COCF(CF_3)_2$ is available as NOVEC 649 from 3M Company, St. Paul, Minn. and is photochemically active in the lower atmosphere and has an atmospheric lifetime of about 5 days. Higher molecular weight perfluorinated nitrogen-containing mono or diketones would be expected to have a similar absorption in the UV spectrum leading to a similar photochemical lifetime with only slight changes expected due to their structure. Provided nitrogen-containing fluorochemical ketones include a first terminal, branched perfluoroalkylcarbonyl group in which said perfluoroalkyl group has from 3 to 10 in-chain carbon atoms which can include, optionally, one or more in-chain oxygen atoms; at least one linear, branched, or cyclic perfluoroalkylene segment having 4 or more in-chain carbon or nitrogen atoms attached to the first terminal, branched perfluoroalkylcarbonyl group, said perfluoroalkylene segment containing one or more in-chain tertiary nitrogen atoms, and a second terminal, branched perfluoroalkylcarbonyl group in which said perfluoroalkyl group has from 3 to 10 in-chain carbon atoms which can include, optionally, one or more in-chain oxygen atoms, wherein the second perfluoroalkylcarbonyl group is attached to the perfluoroalkylene segment or, optionally a fluorochemical nitrogen-containing monoketone compound that comprises a first terminal, substituted or unsubstituted cyclic perfluoroalkyl group in which said cyclic perfluoroalkyl group contains a perfluoropiperazinyl, perfluoropiperidinyl, or perfluoropyrrolidinyl group which said groups may be, optionally, substituted with a perfluoroalkyl group of 1 to 4 carbons or unsubstituted; a linear or branched perfluoroalkylene segment attached to the first terminal cyclic perfluoroalkyl group which has from 1 to 4 carbon atoms and a second terminal, branched heptafluoroisopropylcarbonyl group.

Branched perfluoroalkylcarbonyl groups have perfluoroalkyl groups that include 3 to 10 in-chain carbon atoms. Additionally, the alkyl moieties of the perfluoroalkylcarbonyl groups can have branched perfluoroalkyl groups having from 1 to 4 carbon atoms and can also include one or more in-chain oxygen groups.

The provided nitrogen-containing fluorochemical ketones include one or two carbonyl groups. Provided fluorochemical nitrogen-containing diketones typically have terminal perfluoroalkylcarbonyl groups on each end of a linear, branched or cyclic perfluoroalkylene segment having 4 or more in-chain carbon or nitrogen atoms attached substantially between the two terminal perfluoroalkyl carbonyl groups, said perfluoroalkylene segment containing one or more in-chain tertiary nitrogen atoms. In some embodiments, the provided diketones are symmetrical molecules of the A-B-A structure where A is the perfluoroalkylcarbonyl group and B is the perfluoroalkylene segment. Provided fluorochemical, nitrogen-containing monoketones have a perfluoroalkyl group which contains a perfluoropiperazinyl, perfluoropiperidinyl, or perfluoropyrrolidinyl group which said groups may be, optionally, substituted with a perfluoroalkyl group of 1 to 4 carbons. The provided nitrogen-containing fluorochemical ketones have a chemical structure comprising:

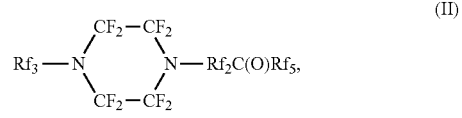

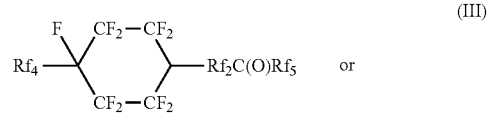

$Rf_1$ represents a perfluoroalkyl group of 3 to 10 carbon atoms that is branched or cyclic or a combination thereof, that optionally contains at least one in-chain oxygen; $Rf_2$ is a linear or branched perfluorinated alkylene group of 1 to 4 carbons; $Rf_3$ is a linear or branched perfluoroalkyl group of 1 to 4 carbons or —$Rf_2C(O)Rf_5$; $Rf_4$ is F— or a linear or branched perfluoroalkyl group of 1 to 4 carbons; $Rf_5$ is $(CF_3)_2CF$—. Exemplary $Rf_1$ groups include $(CF_3)_2CF$—, $C_3F_7OCF(CF_3)$—, $CF_3OC_3F_6OCF(CF_3)$—, $C_4F_9OCF(CF_3)$— and $CF_3OCF(CF_3)$—. In some embodiments, the provided fluorochemical ketones comprise:

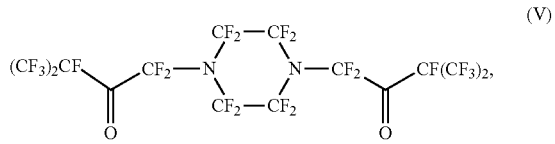

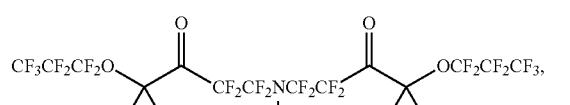

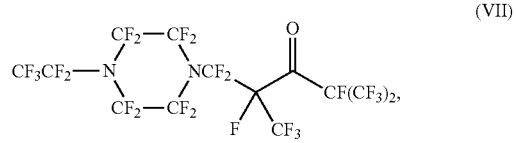

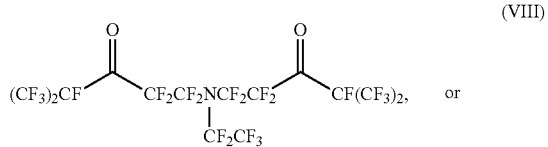

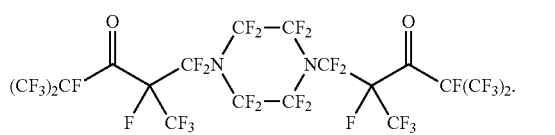

In some embodiments, an apparatus is provided that requires heat transfer. The apparatus includes a device and a mechanism for transferring heat to or from the device using a heat-transfer fluid. Exemplary apparatuses include refrigeration systems, cooling systems, testing equipment, and machining equipment. Other examples include test heads used in automated test equipment for testing the performance of semiconductor dice; wafer chucks used to hold silicon wafers in ashers, steppers, etchers, PECVD tools; constant temperature baths, and thermal shock test baths. In yet other embodiments, the provided apparatus can include a refrigerated transport vehicle, a heat pump, a supermarket food cooler, a commercial display case, a storage warehouse refrigeration system, a geothermal heating system, a solar heating system, an organic Rankine cycle device, and combinations thereof.

In certain embodiments, the provided apparatus includes a device. The device is defined herein as a component, workpiece, assembly, etc. to be cooled, heated or maintained at a selected temperature. Such devices include electrical components, mechanical components and optical components. Examples of devices of the present invention include, but are not limited to microprocessors, wafers used to manufacture semiconductor devices, power control semiconductors, electrical distribution switch gear, power transformers, circuit boards, multi-chip modules, packaged and unpackaged semiconductor devices, lasers, chemical reactors, fuel cells, and electrochemical cells. In some embodiments, the device can include a chiller, a heater, or a combination thereof. In other embodiments, the device can include an electronic component to be soldered and solder. Typically, the heat required for soldering can be supplied by a vapor phase that has a temperature of greater than 170° C., greater than 200° C., greater than 230° C., or even greater.

In certain embodiments, the present disclosure includes a mechanism for transferring heat. Heat is transferred by placing the heat transfer mechanism in thermal contact with the device. The heat transfer mechanism, when placed in thermal contact with the device, removes heat from the device or provides heat to the device, or maintains the device at a selected temperature. The direction of heat flow (from device or to device) is determined by the relative temperature difference between the device and the heat transfer mechanism.

The heat transfer mechanism may include facilities for managing the heat-transfer fluid, including, but not limited to pumps, valves, fluid containment systems, pressure control systems, condensers, heat exchangers, heat sources, heat sinks, refrigeration systems, active temperature control systems, and passive temperature control systems. Examples of suitable heat transfer mechanisms include, but are not limited to, temperature controlled wafer chucks in PECVD tools, temperature controlled test heads for die performance testing, temperature controlled work zones within semiconductor process equipment, thermal shock test bath liquid reservoirs, and constant temperature baths. In some systems, such as etchers, ashers, PECVD chambers, vapor phase soldering devices, and thermal shock testers, the upper desired operating temperature may be as high as 170° C., as high as 200° C., or even higher.

The heat transfer mechanism includes the provided heat-transfer fluid. The provided heat transfer fluid can be represented by nitrogen-containing fluorochemical ketones having a chemical structure:

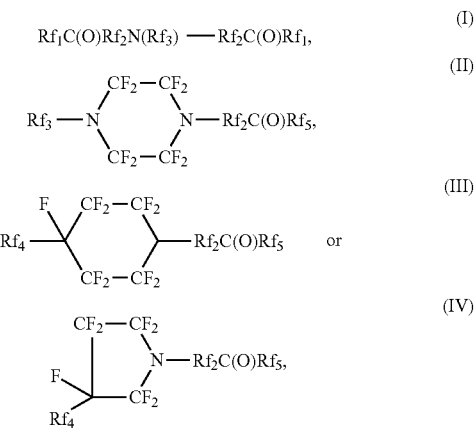

$Rf_1$ represents a perfluoroalkyl group of 3 to 10 carbon atoms that is branched or cyclic or a combination thereof, that optionally contains at least one in-chain oxygen; $Rf_2$. is a linear or branched perfluorinated alkylene group of 1 to 4 carbons; $Rf_3$ is a linear or branched perfluoroalkyl group of 1 to 4 carbons or —$Rf_2C(O)Rf_5$; $Rf_4$ is F— or a linear or branched perfluoroalkyl group of 1 to 4 carbons; $Rf_5$ is $(CF_3)_2$CF—. Exemplary $Rf_1$ groups include $(CF_3)_2CF$—, $C_3F_7OCF(CF_3)$—, $CF_3OC_3F_6OCF(CF_3)$—, $C_4F_9OCF(CF_3)$— and $CF_3OCF(CF_3)$—.

The provided apparatuses and heat transfer fluids fulfill a market need for a high temperature heat transfer fluid. The provided nitrogen-containing fluorochemical ketones provide a stable, high temperature heat transfer fluid. In some embodiments, the provided nitrogen-containing fluorochemical ketones provide a stable, high temperature heat transfer fluid that does not substantially change in purity as measured by gas chromatography/mass spectrometry (CG/MS) when heated and maintained at a temperature of 231° C. for at least 7 days.

In one embodiment, the devices can include equipment that is used to test the performance of semiconductor dice. The dice are the individual "chips" that are cut from a wafer of semiconductor substrate. The dice come from the semiconductor foundry and must be checked to ensure they meet functionality requirements and processor speed requirements. The test is used to sort "known good dice" (KGD) from dice that do not meet the performance requirements. This testing is generally performed at temperatures ranging from about −80° C. to about 100° C.

In some cases, the dice are tested one-by-one, and an individual die is held in a chuck. This chuck provides, as part of its design, provision for cooling the die. In other cases, several dice are held in the chuck and are tested either sequentially or in parallel. In this situation, the chuck provides cooling for several dice during the test procedure. It may be advantageous to test dice at elevated temperatures to determine their performance characteristics under conditions of elevated temperature. In this case, a heat-transfer fluid which has good cooling properties well above room temperature is advantageous. In some cases, the dice are tested at very low temperatures. For example, complementary metal-oxide semiconductor ("CMOS") devices in particular operate more quickly at lower temperatures. If a piece of automated testing equipment (ATE) employs CMOS devices "on board" as part of its permanent logic hardware, it may be advantageous to maintain the logic hardware at a low temperature.

Therefore, to provide maximum versatility to the ATE, a heat-transfer fluid typically performs well at both low and high temperatures (i.e., typically has good heat transfer properties over a wide temperature range), is inert (i.e., is non-flammable, low in toxicity, non-chemically reactive), has high dielectric strength, has a low environmental impact, and has predictable heat-transfer properties over the entire operating temperature range.

In another embodiment, the devices can include etchers. Etchers can operate over temperatures ranging from about 70° C. to about 150° C. Typically, during etching, a reactive plasma is used to anisotropically etch features into a semiconductor. The semiconductor can include a silicon wafer or include a II-VI or a III-V semiconductor. In some embodiments, the semiconductor materials can include, for example, III-V semiconductor materials such as, for example, GaAs, InP, AlGaAs, GaInAsP, or GaInNAs. In other embodiments, the provided process is useful for etching II-VI semiconductor materials such as, for example, materials that can include cadmium, magnesium, zinc, selenium, tellurium, and combinations thereof. An exemplary II-VI semiconductor material can include CdMgZnSe alloy. Other II-VI semiconductor materials such as CdZnSe, ZnSSe, ZnMgSSe, ZnSe, ZnTe, ZnSeTe, HgCdSe, and HgCdTe can also be etched using the provided process. The semiconductors to be processed are typically kept at a constant temperature. Therefore, the heat-transfer fluid that can have a single phase over the entire temperature range is typically used. Additionally, the heat-transfer fluid typically has predictable performance over the entire range so that the temperature can be precisely maintained.

In other embodiments, the devices can include ashers that operate over temperatures ranging from about 40° C. to about 150° C. Ashers are devices that can remove the photosensitive organic masks made of positive or negative photoresists. These masks are used during etching to provide a pattern on the etched semiconductor.

In some embodiments, the devices can include steppers that can operate over temperatures ranging from about 40° C. to about 80° C. Steppers are an essential part of photolithography that is used in semiconductor manufacturing where reticules needed for manufacturing are produced. Reticules are tools that contain a pattern image that needs to be stepped and repeated using a stepper in order to expose the entire wafer or mask. Reticules are used to produce the patterns of light and shadow needed to expose the photosensitive mask. The film used in the steppers is typically maintained within a temperature window of +/−0.2° C. to maintain good performance of the finished reticule.

In yet other embodiments, the devices can include plasma enhanced chemical vapor deposition (PECVD) chambers that can operate over temperatures ranging from about 50° C. to about 150° C. In the process of PECVD, films of silicon oxide, silicon nitride, and silicon carbide can be grown on a wafer by the chemical reaction initiated in a reagent gas mixture containing silicon and at least any one of oxygen, nitrogen, or carbon. The chuck on which the wafer rests is kept at a uniform, constant temperature at each selected temperature.

In yet other embodiments, the devices can include electronic devices, such as processors, including microprocessors. As these electronic devices become more powerful, the amount of heat generated per unit time increases. Therefore, the mechanism of heat transfer plays an important role in processor performance. The heat-transfer fluid typically has good heat transfer performance, good electrical compatibility (even if used in "indirect contact" applications such as those employing cold plates), as well as low toxicity, low (or non-) flammability and low environmental impact. Good electrical compatibility requires the heat-transfer fluid candidate to exhibit high dielectric strength, high volume resistivity, and poor solvency for polar materials. Additionally, the heat-transfer fluid must exhibit good mechanical compatibility, that is, it must not affect typical materials of construction in an adverse manner.

The provided device is defined herein as a component, work-piece, assembly, etc. to be cooled, heated or maintained at a selected temperature. Such devices include electrical components, mechanical components and optical components. Examples of devices of the present invention include, but are not limited to microprocessors, wafers used to manufacture semiconductor devices, power control semiconductors, electrical distribution switch gear, power transformers, circuit boards, multi-chip modules, packaged and unpackaged semiconductor devices, chemical reactors, fuel cells, and lasers.

The provided apparatus includes a mechanism for transferring heat. Heat is transferred by placing the heat transfer mechanism in thermal contact with the device. The heat transfer mechanism, when placed in thermal contact with the device, removes heat from the device or provides heat to the device, or maintains the device at a selected temperature. The direction of heat flow (from device or to device) is determined by the relative temperature difference between the device and the heat transfer mechanism. The provided apparatus can also include refrigeration systems, cooling systems, testing equipment and machining equipment. In some embodiments, the provided apparatus can be a constant temperature bath or a thermal shock test bath.

The heat transfer mechanism includes a provided heat-transfer fluid. Additionally, the heat transfer mechanism may include facilities for managing the heat-transfer fluid, including, but not limited to: pumps, valves, fluid containment systems, pressure control systems, condensers, heat exchangers, heat sources, heat sinks, refrigeration systems, active temperature control systems, and passive temperature control systems. Examples of suitable heat transfer mechanisms include, but are not limited to, temperature controlled wafer chucks in PECVD tools, temperature-controlled test heads for die performance testing, temperature controlled work zones within semiconductor process equipment, thermal shock test bath liquid reservoirs, and constant temperature baths. Constant temperature baths are typically operated over a broad temperature range. Therefore, desirable heat-transfer fluids preferably have a wide liquid range and good low-temperature heat transfer characteristics. A heat-transfer fluid having such properties allows a very wide operating range for the constant temperature bath. Typically, most testing fluids require fluid change-out for wide temperature extremes. Also, good temperature control is essential for accurately predicting physical properties of the heat-transfer fluids.

In other aspects, a method of transferring heat is provided that includes providing a device and transferring heat to or from the device using a mechanism. The mechanism can include a heat transfer fluid such as the nitrogen-containing fluorochemical ketones disclosed herein. The provided method can include vapor phase soldering wherein the device is an electronic component to be soldered.

Objects and advantages of this invention are further illustrated by the following examples, but the particular materials and amounts thereof recited in these examples, as well as other conditions and details, should not be construed to unduly limit this invention

EXAMPLES

Unless otherwise noted, all solvents and reagents may be obtained from Aldrich Chemical Co. of Milwaukee, Wis. As used herein, "NOVEC-7200" refers to ethyl perfluorobutyl ether and is available from 3M Company, St. Paul, Minn. Also as used herein "HFPO" refers to hexafluoropropene oxide and "HFP" refers to hexafluoropropene. "Diglyme" refers to diethylene glycol dimethyl ether.

Example 1

Preparation of 1,1'-(perfluoropiperazine-1,4-diyl)bis(1,1,3,4,4,4-hexafluoro-3-(trifluoromethyl)butan-2-one). (V)

Preparation of Intermediate: (4-ethoxycarbonylmethyl-piperazine-1-yl)acetic acid ethyl ester A five liter three-necked round bottom flask was equipped with an overhead stirrer, water condenser, thermometer and addition funnel and the apparatus placed under a nitrogen atmosphere using a glass tee on top of the condenser. Into the flask were placed, piperazine (230.9 g, 2.68 mol, Aldrich), methyl t-butyl ether (2.0 l) and isopropanol (280 g). The mixture was heated to 50° C. and ethyl chloroacetate ($ClCH_2CO_2Et$, 658 g, 5.37 mol, Aldrich) added rapidly dropwise. An additional 150 mL of isopropanol was added to keep the mixture fluid midway through this addition. Near the end of the ethyl chloroacetate addition, triethylamine (542 g, 5.37 mol, Aldrich) was added rapidly dropwise to take up the HCl formed in the reaction and the reaction mixture heated to 55° C. for 16 hours. The reaction mixture was cooled and the solid triethylamine hydrochloride filtered and the filter cake washed once with methyl t-butyl ether. The ether was removed by rotary evaporation and the residue distilled under vacuum 140-150° C./2 mm Hg giving a product of 97% purity. This material was combined with two other preparations and subjected to electrochemical fluorination in a Simons ECF cell of essentially the type described in U.S. Pat. No. 2,713,593 (Brice et al.) and in R. E. Banks, *Preparation, Properties and Industrial Applications of Organofluorine Compounds*, pages 19-43, Halsted Press, New York (1982) to afford after distillation 2,2'-(perfluoropiperazine-1,4-diyl)bis(2,2-difluoroacetyl fluoride).

2,2'-(perfluoropiperazine-1,4-diyl)bis(2,2-difluoroacetyl fluoride) (70% purity, 140 g 0.33 mol), potassium fluoride (9.57 g 0.16 mol) and diglyme (270 g) were combined in a 600 mL Parr reactor. The reactor was sealed and the mix was heated to 75° C. Hexafluoropropene (100 g 0.66 mol, MDA) was added as a gas to the reaction mixture. The reaction mixture was then stirred for 18 hours to allow for maximum reaction of the di-acid fluoride to react with the hexafluoropropene. After 18 hours, the reaction mix was cooled to room temperature and the salts were removed through vacuum filtration. The liquid was then transferred to a separatory funnel where the lower fluorochemical phase was separated from the diglyme phase. The crude product was purified by fractional distillation using a concentric tube column. The final sample purity was 91.4% by GC-FID. The product mass was confirmed by GC/MS. The boiling point of the product at 760 mmHg was measured to be 209° C.

Example 2

Preparation of 5,5'-((trifluoromethyl)azanediyl)bis(1,1,1,2,4,4,5,5-octafluoro-2-perfluoropropoxy)pentan-3-one). (VI)

Preparation of Intermediate: $CH_3N(CH_2CH_2CO_2CH_3)_2$

Into a 3 L round bottom flask cooled in a water bath and equipped with an overhead stirrer, thermometer, gas inlet tube and a solid carbon dioxide/acetone filled condenser under a nitrogen atmosphere were placed 4-methoxyphenol (Aldrich, 3.5 g) and methyl acrylate (Aldrich, 907 g, 10.5 mol). Methylamine (Aldrich, 163 g, 5.25 mol) was added slowly over about two hours through the gas inlet tube keeping the temperature less than about 30° C. After the addition was complete, the reaction mixture was stirred for 16 hours at ambient temperature. The excess methyl acrylate and much of the 1:1 addition product were then distilled from the reaction mixture under a vacuum of 3 mm Hg giving a final product purity of 96.6% the desired $CH_3N(CH_2CH_2CO_2CH_3)_2$.

Preparation of $CF_3N(CF_2CF_2COF)_2$

This material was prepared by the electrochemical fluorination of $CH_3N(CH_2CH_2CO_2CH_3)_2$ in a Simons ECF cell of the type described in U.S. Pat. No. 2,713,593 (Brice et al.) and in R. E. Banks, *Preparation, Properties and Industrial Applications of Organofluorine Compounds*, pages 19-43, Halsted Press, New York (1982). Purification by fractional distillation gave material in a purity of 94.7% as determined by GC-FID and GC/MS analysis.

$CF_3N(CF_2CF_2COF)_2$ (240 g 0.636 mol), cesium fluoride (Aldrich, 77 g 0.51 mol), perfluoropropyl vinyl ether (Dyneon 618 g, 2.32 mol) and diglyme solvent (400 mL) were combined in a 2 L Parr pressure reactor. The reactor was sealed and heated to 65° C. for 72 hours. After 72 hours, the mix was cooled and a sample was analyzed by GC-FID. GC-FID indicated conversion of 87%. The product mix was filtered from the cesium fluoride salts and transferred to a 1 L separatory funnel. The lower fluoroketone product phase was removed from the diglyme solvent. This fluoroketone phase was passed through a column of silica gel to remove residual diglyme. The ketone was then purified using fractional distillation with a 20-tray Oldershaw column. The product mass was verified by GC/MS and the structure and purity were confirmed by $^1H$ and $^{19}F$ NMR. The purity of this sample was 98.9%. The boiling point at 760 mm Hg was measured as 231° C.

Example 3

Preparation of

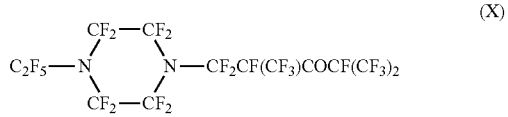

(X)

Preparation of Intermediate

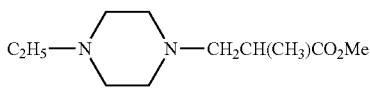
(XI)

1-ethylpiperazine (570 g, 5.0 mol, Aldrich) was added dropwise rapidly to a solution of methyl methacrylate (500 g, 5.0 mol, Aldrich) in methanol (375 mL) at 55° C. After the addition was completed, the reaction mixture was held at 55° C. for 16 hours. An additional 50 g of methyl methacrylate was added and the reaction mixture heated to 65° C. for an additional 16 hours. The methanol and most of the excess methyl methacrylate were removed by rotary evaporation and the residue distilled under vacuum (105-110° C./4 mmHg) to afford 1051 g of >99% purity ester (XI) which was then subjected to ECF essentially as described in Example 1 to give the perfluorinated acyl fluoride product (XII) which was purified further by distillation (bp=158° C., 90% purity).

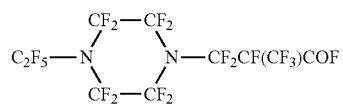
(XII)

The distilled acid fluoride (75 g, 90% purity, 0.124 mol), cesium fluoride (6.21 g, 0.041 mol, Aldrich) and anhydrous diglyme (28 g, Aldrich) were added to a 600 mL Parr reactor, the reactor sealed and degassed under nitrogen and heated to 40° C. Hexafluoropropylene (66.4 g, 0.44 mol, 3M, St. Paul, Minn.) was added in several portions over two hours and then held for an additional 88 hours at 40° C. The reactor was then cooled, any excess hexafluoropropylene vented and the lower fluorochemical phase separated from the diethylene glycol dimethyl ether solvent and distilled to yield the ketone product in 95% purity (bp=200° C.). The product mass was confirmed by GC/MS. The IR of the ketone showed a carbonyl absorption at 1770 cm$^{-1}$.

Example 4

Preparation of

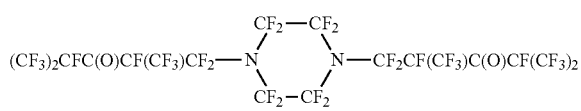
(IX)

Preparation of Intermediate

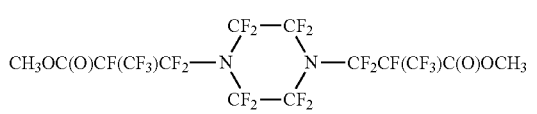
(XIII)

Piperazine (502 g, 5.84 mol, Aldrich) was added dropwise rapidly to a solution of methyl methacrylate (1284 g, 12.84 mol mol, Aldrich) in methanol (432 g) at about 60° C. After the addition was completed, the temperature was increased to 70° C. and the reaction mixture held at that temperature for 18 hours. The methanol and most of the excess methyl methacrylate were removed by rotary evaporation and the residue distilled under vacuum (discarding all material boiling less than 155° C./0.1 mmHg) to afford the ester in 95% purity which was then subjected to ECF essentially as described in Example 1 to give the perfluorinated acyl fluoride product which was purified further by distillation of the lower boiling point impurities. The acid fluoride product was a solid.

The acid fluoride (126.5 g of about 90% purity), cesium fluoride (18.2 g, 0.12 mol) and diglyme (50 g) were combined in a 600 mL Parr reactor, the reactor sealed and degassed under nitrogen and then heated to 40° C. Hexafluoropropylene (90 g, 0.6 mol, 3M) was added in several portions over five hours and then held for an additional 68 hours at 40° C. The reactor was then cooled, the excess hexafluoropropylene vented and the cesium fluoride solids filtered. The lower fluorochemical phase was separated from the solvent and this material (132 g) was placed in a 600 mL Parr reaction vessel along with cesium fluoride (10 g) and diglyme (27 g) and the reaction repeated with the addition of a large excess of HFP (210 g) as described. After workup as described the lower fluorochemical phase was analyzed and found to contain about 6.3% of the desired ketone by GC/MS. The ketone was distilled to a purity of 83% (bp >218° C.).

Example 5

Preparation of $C_2F_5N[CF_2CF_2C(O)CF(CF_3)]_2$

Preparation of Intermediate: $C_2H_5N(CH_2CH_2CO_2CH_3)_2$

The dimethyl ester was prepared by the addition of two moles of methyl acrylate to ethylamine in a procedure essentially as described in Example 2 for the addition methylamine with two moles of methyl methacrylate.

Preparation of $C_2F_5N(CF_2CF_2COF)_2$

This material was prepared by the electrochemical fluorination of $C_2H_5N(CH_2CH_2CO_2CH_3)_2$ in a Simons ECF cell of the type described in U.S. Pat. No. 2,713,593 (Brice et al.) and in R. E. Banks, *Preparation, Properties and Industrial Applications of Organofluorine Compounds*, pages 19-43, Halsted Press, New York (1982). Purification by fractional distillation gave material in a purity of 76% as determined by GC-FID and GC/MS analysis.

A clean dry 600 mL stainless steel Parr pressure reactor was charged with spray-dried potassium fluoride (3.4 g), anhydrous diglyme (180 g), NOVEC-7200 (124 g) and $C_2F_5N(CF_2CF_2COF)_2$ (165 g). The vessel was sealed and heated to 76° C. HFP (112.5 g) was added over seven hours and the reaction stirred for an additional 16 hours. A second charge of HFP (58.5 g) was then added over seven hours and the reaction held at 76° C. for 16 hours. The mixture was cooled to room temperature and transferred to a 1 liter round bottom flask set up for a 40 mmHg vacuum one-plate distillation and the mixture was heated to 75° C. to remove NOVEC-7200. The flask was cooled to ambient temperature and transferred to a 500 ml separatory funnel. After about an hour the lower fluorochemical phase was separated and washed two times with approximately equal volumes of water to obtain the bottom product phase (216 g) in 82.8% purity. Purification by atmospheric fractionation afforded material with a purity of 97.1% $C_2F_5N[CF_2CF_2C(O)CF(CF_3)_2]_2$ as determined by GC-FID, GC/MS, $^1$H-NMR and $^{19}$F-NMR analysis.

Stability Testing of $C_3F_7OCF(CF_3)C(O)CF_2CF_2N$
$(CF_3)CF_2CF_2C(O)CF(CF_3)OC_3F_7$ 50 mL sample of $C_3F_7OCF(CF_3)C(O)CF_2CF_2N(CF_3)$ $CF_2CF_2C(O)CF(CF_3)OC_3F_7$ was refluxed at its atmospheric boiling point of 231° C. for 7 days in the presence of 0.73 g of AMTECH NC559AS solder with flux. An identical sample without solder was also refluxed for 7 days. These fluids were analyzed by GCFID for relative purity:

TABLE 1

| Sample ID | GCFID relative purity |
| --- | --- |
| 1. Example 2 (+ solder) VPS test | 98.6984 |
| 2. Example 2 (−solder) VPS test | 98.5048 |
| 3. Example 2 virgin sample (+solder) | 98.5873 |
| 4. Example 2 virgin sample (−solder) | 98.5058 |

The results of fluoride analysis summarized in Table 2 below.

TABLE 2

| Sample ID | ppm Fluoride (w/v) |
| --- | --- |
| 1. Example 2 (+solder) VPS test | 2.3 ± 0.01 |
| 2. Example 2 (−solder) VPS test | 13.8 ± 0.6 |
| 3. Example 2 virgin sample (−solder) | 2.68* |

*Insufficient sample to analyze in duplicate.

Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein as follows. All references cited in this disclosure are herein incorporated by reference in their entirety.

What is claimed is:

1. A fluorochemical nitrogen-containing diketone compound comprising:
   a first terminal, branched perfluoroalkylcarbonyl group having from 3 to 10 in-chain carbon which can include, optionally, one or more in-chain oxygen atoms;
   at least one linear, branched, or cyclic perfluoroalkylene segment having 4 or more in-chain carbon or nitrogen atoms attached to the first terminal, branched perfluoroalkylcarbonyl group, said perfluoroalkylene segment containing one or more in-chain tertiary nitrogen atoms; and
   a second terminal, branched perfluoroalkylcarbonyl group having from 3 to 10 in-chain carbon atoms which can include, optionally, one or more in-chain oxygen atoms, wherein the second perfluoroalkylcarbonyl group is attached to the perfluoroalkylene segment.

2. A fluorochemical nitrogen-containing diketone compound according to claim 1, wherein the first terminal, branched perfluoroalkylcarbonyl group, the second terminal, branched perfluoroalkylcarbonyl group, or both include at least one in-chain oxygen atom.

3. A fluorochemical nitrogen-containing diketone compound according to claim 1, comprising a second terminal, branched perfluoroalkylcarbonyl group having from 3 to 10 in-chain carbon or oxygen atoms which can include, optionally, an in-chain oxygen atom, wherein the second terminal, branched perfluoroalkylcarbonyl group is attached to the perfluoroalkylene segment.

4. A fluorochemical nitrogen-containing diketone compound according to claim 1, wherein the perfluoroalkylene segment includes a perfluoropiperazinyl, perfluoropiperidinyl, or a perfluoropyrrolidnyl group.

5. A fluorochemical nitrogen-containing diketone compound according to claim 1 having a boiling point at ambient pressure of 170° C. or greater.

6. A fluorochemical nitrogen-containing monoketone comprising:
   a first terminal, substituted or unsubstituted cyclic perfluoroalkyl group, said perfluoroalkyl group comprising a perfluoropiperazinyl, perfluoropiperidinyl, or a perfluoropyrrolidinyl group, having from 8 to 15 in-chain carbon or nitrogen atoms;
   a linear or branched perfluoroalkylene segment, having 1 to 4 carbon atoms attached to the first terminal cyclic perfluoroalkyl group; and
   a second terminal branched heptafluoroisopropylcarbonyl group.

7. A fluorochemical nitrogen-containing monoketone according to claim 6, wherein the perfluoropiperazinyl, perfluoropiperidinyl, perfluoropyrrolidinyl, or a combination thereof are substituted with a perfluoroalkyl group having from 1 to 4 carbon atoms.

8. A fluorochemical nitrogen-containing diketone compound according to claim 6 having a boiling point at ambient pressure of 170° C. or greater.

9. A compound according to claim 6 selected from the group consisting of

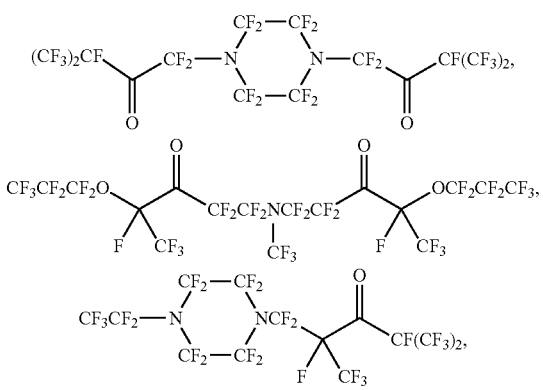

-continued

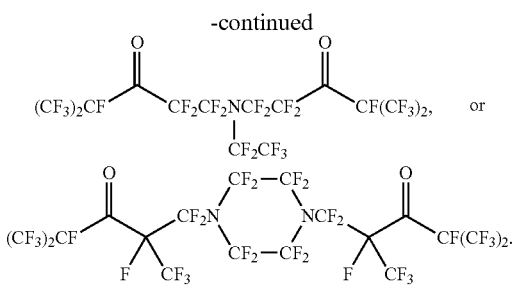

and combinations thereof.

10. An apparatus for heat transfer comprising:
a device; and
a mechanism for transferring heat to or from the device, the mechanism comprising a heat transfer fluid that includes one or both of:
a) a fluorochemical nitrogen-containing diketone compound comprising:
   a first terminal, branched perfluoroalkylcarbonyl group having from 3 to 10 in-chain carbon atoms;
   at least one linear, branched, or cyclic perfluoroalkylene segment having 4 or more in-chain carbon or nitrogen atoms attached to the first terminal, branched perfluoroalkylcarbonyl group, said perfluoroalkylene segment containing one or more in-chain tertiary nitrogen atoms; and
   a second terminal, branched perfluoroalkylcarbonyl group having from 3 to 10 in-chain carbon atoms,
wherein the second perfluoroalkylcarbonyl group is attached to the perfluoroalkylene segment,
b) a fluorochemical nitrogen-containing monoketone compound that comprises:
   a first terminal, substituted or unsubstituted cyclic perfluoroalkyl group, said cyclic perfluoroalkyl group comprising a perfluoropiperazinyl, perfluoropiperidinyl, or perfluoropyrrolidinyl group;
   a linear or branched perfluoroalkylene segment attached to the first terminal cyclic perfluoroalkyl group, said cyclic perfluoroalkyl group having from 1 to 4 carbon atoms; and
   a second terminal branched heptafluoroisopropylcarbonyl group, or a combination thereof.

11. An apparatus for heat transfer according to claim 10, wherein the first terminal, branched perfluoroalkylcarbonyl group includes one or more in-chain oxygen atoms.

12. An apparatus for heat transfer according to claim 10, wherein the second terminal, branched perfluoroalkylcarbonyl group includes one or more in-chain oxygen atoms.

13. An apparatus for heat transfer according to claim 10, wherein the perfluoropiperazinyl, perfluoropiperidinyl, or perfluoropyrrolidinyl group is substituted with a perfluoroalkyl group having 1 to 4 carbon atoms.

14. An apparatus according to claim 10, wherein the device is selected from a microprocessor, a semiconductor wafer used to manufacture a semiconductor device, a power control semiconductor, an electrochemical cell (including a lithium-ion cell), an electrical distribution switch gear, a power transformer, a circuit board, a multi-chip module, a packaged or unpackaged semiconductor device, a fuel cell, and a laser.

15. An apparatus according to claim 10, wherein the mechanism transfers heat to the device.

16. An apparatus according to claim 10, wherein the mechanism transfers heat from the device.

17. An apparatus according to claim 10 wherein the mechanism maintains the device at a selected temperature.

18. An apparatus according to claim 10, wherein the apparatus comprises refrigeration systems, cooling systems, testing equipment, and machining equipment.

19. An apparatus according to claim 10, wherein the device comprises an electronic component to be soldered and solder.

20. An apparatus according to claim 19, wherein the mechanism comprises vapor phase soldering.

21. A method of transferring heat comprising:
providing a device; and
transferring heat to or from the device using a mechanism, the mechanism comprising:
   a heat transfer fluid,
wherein the heat transfer fluid includes a fluorochemical ketone compound according to claim 1.

22. A method of vapor phase soldering according to claim 21, wherein the device is an electronic component to be soldered.

* * * * *

UNITED STATES PATENT AND TRADEMARK OFFICE
CERTIFICATE OF CORRECTION

| | | |
|---|---|---|
| PATENT NO. | : 8,535,559 B2 | Page 1 of 2 |
| APPLICATION NO. | : 12/732608 | |
| DATED | : September 17, 2013 | |
| INVENTOR(S) | : Richard Flynn | |

It is certified that error appears in the above-identified patent and that said Letters Patent is hereby corrected as shown below:

On the Title Page

Column 1, Item (75) fifth inventor city name
Line 5, delete "Fanbault" and insert -- Fairbault --, therefor.

Column 2, Item (56) References Cited, Other Publications
Line 9, delete ""Appartus" and insert -- "Apparatus --, therefor.

In the Specification

Column 10
Line 67, delete "invention" and insert -- invention. --, therefor.

Column 13
Lines 17-26, delete "50 g…………..purity)." and insert the same on Col. 13, Line 16 after "additional" as a continuation of same paragraph.

Column 14
Line 14, delete "mol mol," and insert -- mol, --, therefor.

In the Claims

Column 16
Line 22, in Claim 4, delete "perfluoropyrrolidnyl" and insert -- perfluoropyrrolidinyl --, therefor.

Signed and Sealed this
Ninth Day of September, 2014

Michelle K. Lee
*Deputy Director of the United States Patent and Trademark Office*

CERTIFICATE OF CORRECTION (continued)
U.S. Pat. No. 8,535,559 B2

Column 17

Lines 1-6, in Claim 9, delete "or" after  .

Lines 7-11, in Claim 9, delete " 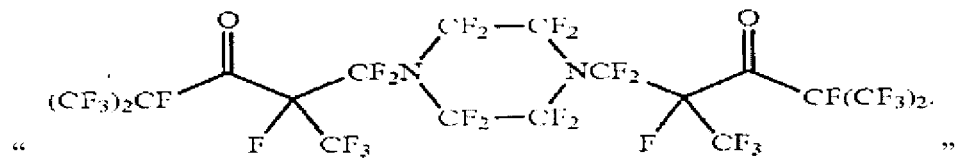 "

and insert -- 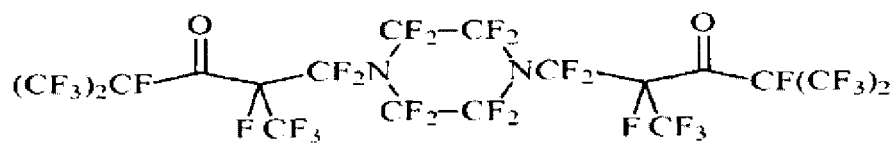 --, therefor.